United States Patent [19]

Chen et al.

[11] Patent Number: 6,025,206

[45] Date of Patent: Feb. 15, 2000

[54] METHOD FOR DETECTING DEFECTS

[75] Inventors: Jain-Hon Chen, Chiayi; Chi-Fa Ku, Hsinchu Hsien; Li-Dar Tsai, Tainan, all of Taiwan

[73] Assignee: United Microelectronics Corp., Hsin-Chu, Taiwan

[21] Appl. No.: 09/080,085

[22] Filed: May 15, 1998

[30] Foreign Application Priority Data

Mar. 12, 1998 [TW] Taiwan ................................. 87103639

[51] Int. Cl.$^7$ ........................... G01R 31/26; H01L 21/66; G01N 21/00; G01N 21/86
[52] U.S. Cl. ..................... 438/16; 250/559.41; 356/237.3
[58] Field of Search ................... 250/559.41; 356/237.3; 438/7, 16

[56] References Cited

U.S. PATENT DOCUMENTS 4,965,454 10/1990 Yamauchi et al. ...................... 356/237
5,715,052 2/1998 Fujino et al. .......................... 356/237

*Primary Examiner*—Brian Dutton

[57] ABSTRACT

A method for detecting defects comprises scanning a clean blank wafer for figuring out the quantity and locations of particles; then, scanning the wafer again after performing coating, exposure, and development processes on the wafer; comparing the two scanning results for figuring out the locations of the defects and calculating quantities of the defects by checking the patterns and colors, and then to obtain the quantities and types of the defects in mechanisms and photoresist respectively.

13 Claims, No Drawings

METHOD FOR DETECTING DEFECTS

CROSS-REFERENCE TO RELATED APPLICATION

This application claims the priority benefit of Taiwan application serial no. 87103639, filed Mar. 12, 1998, the full disclosure of which is incorporated herein by reference.

BACKGROUND OF THE INVENTION

1. Field of the Invention

This invention relates to a method for detecting and testing wafers during a semiconductor fabrication process, and more particularly, to a method for detecting and analyzing defects on wafers during the semiconductor fabrication process.

2. Description of Related Art

As a result of the downsizing of the designed line width, to improve and maintain the yield of semiconductor fabrication process has become more and more difficult. Among defects on wafers, the particles and defects are the most critical ones for the yield of semiconductor fabrication process. Hence, how to detect, analyze, and reduce particles and defects are directly related to the improvement of semiconductor fabrication process.

Generally, both patterned and blank wafers need a plurality of steps of before-process inspection. Before the accomplishment, every wafer needs to be inspected to ensure that every fabricating step is correct and precise, for maintaining a good yield. The inspecting steps include inspecting the quantity of particles generated by the apparatuses of fabrication process, such as chemical vapor deposition.

The conventional method for detecting particle defect on wafers before and after applying photoresist by using the scattering principle of laser beams, is to scan an blank wafer and calculate the quantity of particles, and then, to repeat the step again after photoresist is applied, and finally, to obtain the quantity of particle defects within the photoresist and apparatus by calculating the difference between those two quantities of particles. However, the conventional method can only detect the defects caused by particles, but not the defects formed after the exposure and development of the photoresist. Furthermore, some of those particles detected before the photoresist is applied might be covered by the photoresist after coating and cannot be detected, which will leads to a detecting error.

SUMMARY OF THE INVENTION

It is therefore an objective of the present invention to provide a method for detecting the defects of the wafers and the quantity of particles in the environment of the apparatuses by using the difference of colors and patterns.

In accordance with the foregoing and other objectives of the present invention, the method for detecting defects is firstly scanning a blank wafer and finding the quantity and locations of particles on the wafer, then scanning the wafer again and finding the locations and quantity of defects by checking the discrepant patterns and colors after the photolithography which includes coating, exposure, and development. By comparing the scanning results before and after photolithography process, the quantity and locations of defects on the photoresist and within the apparatus can be then obtained.

DETAILED DESCRIPTION OF PREFERRED EMBODIMENTS

The invention provides a new method for detecting quantity of particles in the coating, exposure, and development mechanisms, and quantity of defects on the photoresist before and after exposure and development in an integrated circuit fabrication.

Firstly, the detecting process starts with scanning a clean blank wafer by such as using Surfscan and applying the principle of diffraction of laser, or using KLA defect scanner and checking the scanned patterns and colors, for figuring out the quantity and locations of particles. Because the particles on the wafer will cause the changes on the frequencies of the scattered laser beam, the laser beam scattered by a particle has a different color from the color shown by the laser beams scattered by the clean portion of the wafer. It is obvious that the clean portion of a wafer is far larger than the portion occupied by the particles. So, the locations of defects or particles can be found by checking the locations of colors or patterns that are different from the majority, and the defective area can be determined by checking the region of changed colors and patterns.

The clean blank wafer is now coated, exposed, and developed in sequence, in order to form a pattern including holes and lines/spacers. Then, the patterned wafer is scanned by KLA optical microscope again. By comparing the scanned patterns and colors in the scanning images before and after the coating, exposure, and development process, the quantity and locations of defects of the photoresist and mechanisms are then determined.

The defects before the coating process are caused by particles. Some of those particles may be covered by photoresist after coating, and cannot be detected by conventional detecting method. The method according to the invention can still detect the particles covered by photoresist and their sizes by applying color comparing. In addition, the method according to the present invention can also detect the defects caused by the difference of patterns after development which include defects caused by defective development on photoresist itself, and defects of pattern difference caused by the particles in photoresist and mechanisms.

The method according to the invention can also observe the types of defects and estimate their sizes by employing a scanning electron microscope. The advantage of the method according to the present invention is to detect the defect caused by the pattern difference after development, in the mean time, to determine the types of defects and estimate the sizes of the defects precisely by employing a scanning electron microscope, which cannot be done by conventional methods. The following table lists the different between the method according to the present invention and conventional methods.

|  | The method according to the present invention | Conventional method |
| --- | --- | --- |
| Principles of detecting | Pattern and color mapping | Scattering of laser beams |
| Objects for detecting | Blank or patterned wafers | Blank wafer |
| Detecting the types of defects | Yes | No |
| Precision of detection | High | Low |
| Detecting defects after development | Yes | No |

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for detecting defects comprising:

scanning a wafer for obtaining a first information indicating a quantity of a plurality of particles on the wafer and a plurality of locations of the particles on the wafer;

coating a photoresist layer on the wafer;

processing exposure and development on the photoresist layer;

scanning the wafer after the development for obtaining a second information indicating a quantity of a plurality of defects on the wafer and a plurality of locations of the defects on the wafer; and comparing the first information and second information for calculating the quantity, types and the locations of the defects.

2. The method of claim 1, wherein the first information shows the locations of the particles by color difference, and sizes and shapes of the particles by patterns.

3. The method of claim 1, wherein the second information shows the locations of the defects by color difference, and sizes and shapes of the defects by patterns.

4. The method of claim 1, wherein the second information shows the locations of the defects by a scanned result of a laser scanner, and sizes and shapes of the defects by patterns.

5. The method of claim 1, wherein a difference of the quantity of the defects minus the quantity of the particles is a quantity of the defects caused by the photoresist itself.

6. The method of claim 1, wherein the method is further combined with a scanning electron microscope for observing the types of the defects and estimating the sizes of the defects precisely.

7. The method of claim 1, wherein the method is used within a photo module.

8. A method for detecting defects which detects a quantity of a plurality of particles within coating, exposure, and development mechanisms in a photo module, and a quantity of a plurality of defects after coating, exposure, and development process, comprising:

scanning a clean wafer for a first information indicating a quantity of a plurality of particles and a plurality of locations of the particles;

coating the wafer with a photoresist layer;

processing exposure and development on the wafer for forming a desired pattern;

scanning the desired pattern for obtaining a second information indicating a quantity of a plurality of defects and a plurality of locations of the defects; and comparing the patterns and the difference between the quantities in the first information and the second information.

9. The method of claim 8, wherein the first information indicates the locations of the particles by color difference, and indicates the sizes and shapes of the particles by the patterns.

10. The method of claim 8, wherein the first information shows the locations of the defects by a scanned result of a laser scanner, and shows sizes and shapes of the defects by patterns.

11. The method of claim 8, wherein the second information indicates the locations of the defects by color difference, and indicates the sizes and shapes of the defects by the pattern.

12. The method of claim 8, a difference of the quantity of the defects minus the quantity of the particles is a quantity of defects caused by the photoresist itself.

13. The method of claim 8, wherein the method is further combined with a scanning electron microscope for observing the types of the defects, and estimating the size of the defects precisely.

* * * * *